(12) United States Patent
Harrison

(10) Patent No.: US 8,639,305 B2
(45) Date of Patent: Jan. 28, 2014

(54) SUPERCONDUCTIVE ELECTROMAGNET APPARATUS AND COOLING APPARATUS AND METHOD THEREOF

(71) Applicant: Samsung Electronics Co., Ltd., Gyeonggi-do (KR)

(72) Inventor: Stephen M Harrison, Wallingford (GB)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 13/649,411

(22) Filed: Oct. 11, 2012

(65) Prior Publication Data

US 2013/0096007 A1    Apr. 18, 2013

(30) Foreign Application Priority Data

Oct. 12, 2011    (KR) .......................... 10-2011-0103990

(51) Int. Cl.
*H01F 6/06* (2006.01)

(52) U.S. Cl.
USPC ......................................................... 505/163

(58) Field of Classification Search
USPC .......................................... 505/163, 211, 879
See application file for complete search history.

(56) References Cited

U.S. PATENT DOCUMENTS

| | | | | |
|---|---|---|---|---|
| 5,317,879 | A * | 6/1994 | Goldberg et al. | 62/51.1 |
| 6,239,957 | B1 * | 5/2001 | McDougall et al. | 361/19 |
| 8,162,037 | B2 * | 4/2012 | Kruip et al. | 165/104.28 |
| 8,238,988 | B2 * | 8/2012 | Stautner | 505/162 |

FOREIGN PATENT DOCUMENTS

| | | |
|---|---|---|
| JP | 6-204033 A | 7/1994 |
| JP | 10-144545 A | 5/1998 |
| JP | 10-294213 A | 11/1998 |
| JP | 2002-043117 A | 2/2002 |
| JP | 2007-005793 A | 1/2007 |
| JP | 2010-245524 A | 10/2010 |
| KR | 10-2008-0038021 A | 5/2008 |

* cited by examiner

*Primary Examiner* — Colleen Dunn
(74) *Attorney, Agent, or Firm* — Cha & Reiter, LLC

(57) ABSTRACT

A magnetic resonance imaging apparatus has a plurality of cooling pipes disposed while being spaced apart from each other along a longitudinal length of the coil assembly, a first manifold connected to a lower end of the plurality of cooling pipes to distribute and supply a coolant to the plurality of cooling pipes, and a second manifold connected to an upper end of the plurality of cooling pipes to be supplied with the coolant from the plurality of cooling pipes, thereby able to evenly cool off the coil assembly in a longitudinal direction thereof.

18 Claims, 5 Drawing Sheets

SUPERCONDUCTIVE ELECTROMAGNET APPARATUS AND COOLING APPARATUS AND METHOD THEREOF

CLAIM OF PRIORITY

This application claims, pursuant to 35 U.S.C. 119(a), priority to and the benefit of the earlier filing date of Korean Patent Application No. 2011-0103990, filed on Oct. 12, 2011 in the Korean Intellectual Property Office, the disclosure of which is incorporated herein by reference.

BACKGROUND OF THE INVENTION

1. Field of the Invention

The present invention relates to superconductive electromagnets, and more particularly to a cooling apparatus for a superconductive electromagnet apparatus configured to operate as a superconductive magnet at a cryogenic state.

2. Description of the Related Art

In general, a superconductive electromagnet apparatus is configured to receive an applied electrical current and to generate a strong magnetic field by operating as a superconductive magnet at a cryogenic state.

The superconductive electromagnet apparatus as such includes a coil configured to generate a magnetic field when an electrical current is applied and to operate as a superconductive magnet in a cryogenic state, a housing having a shape of a ring in which the coil is positioned, a helium container in which a coil assembly is positioned and in which helium in a liquid state is retained, and a cryogenic cooling apparatus configured to cool off the helium such that the helium maintains the liquid state.

Thus, when heat is generated from the coil, the helium in a liquid state, which fills an inside of the housing, changes into a gaseous state by absorbing the heat, and the helium in the gaseous state, having a relatively lower density compared to the helium in a liquid state, moves to an upper side of the housing due to the difference of density. The helium in the gaseous state, which moves to the upper side of the housing, is cooled off by the cryogenic cooling apparatus that is disposed at an upper side of an inside of the housing, and so the helium changes again into the liquid state, and thus the coil disposed at an inside of the housing may continuously maintain the cryogenic state.

When using the superconductive electromagnet apparatus, a magnetic resonance imaging apparatus is configured to obtain a cross-sectional image of a body by using a nuclear magnetic resonance phenomenon that occurs due to a strong magnetic field generated from the superconductive electromagnet apparatus, and is referred to as Magnetic Resonance Imaging (MRI).

SUMMARY OF THE INVENTION

Therefore, it is an aspect of the present invention to provide a superconductive electromagnet apparatus capable of evenly cooling off a coil assembly in a longitudinal direction thereof.

It is another aspect of the present invention to provide a superconductive electromagnet apparatus capable of maintaining the coil assembly at a cryogenic state in a stable manner.

Additional aspects of the present invention will be set forth in part in the description which follows and, in part, will be obvious from the description, or may be learned by practice of the present invention.

In accordance with one aspect of the present invention, a superconductive electromagnet apparatus includes a coil assembly and a cooling apparatus. The coil assembly may be configured to be maintained at a cryogenic state. The cooling apparatus may be configured to cool off the coil assembly to a cryogenic state. The cooling apparatus may include a plurality of cooling pipes, a first manifold and a second manifold. The plurality of cooling pipes may be disposed at the coil assembly and supplied with a coolant to absorb the heat generated by the coil assembly. The first manifold may be configured to distribute and supply a coolant to the plurality of cooling pipes. The second manifold may be supplied with a coolant from the plurality of cooling pipes.

The first manifold may be connected to a lower portion of the plurality of cooling pipes, and the second manifold may be connected to an upper portion of the plurality of cooling pipes.

The cooling apparatus may further include a buffer chamber, a cryogenic cooling apparatus, a first circulation pipe and a second circulation pipe. The buffer chamber may have the coolant from the second manifold temporarily stored therein. The cryogenic cooling apparatus may be disposed at the buffer chamber to cool off the coolant. The first circulation pipe may be configured to guide the coolant from the buffer chamber to the first manifold. The second circulation pipe may be configured to guide the coolant from the second manifold to the buffer chamber.

The superconductive electromagnet apparatus may further include a subsidiary cooling apparatus connected to the second circulation pipe. The cooling apparatus may include a first valve disposed at the second circulation pipe. The subsidiary cooling apparatus may include a subsidiary cooling device, an intake pipe, a pump, a discharging pipe, and a second valve. The subsidiary cooling device may be configured to cool off the coolant. The pump may be configured to pump the coolant. The intake pipe may have one end thereof connected to the second circulation pipe between the first valve and the second manifold while the other end thereof is connected to an intake side of the pump. The discharging pipe may have one end thereof connected to the second circulation pipe between the first valve and the buffer chamber while the other end thereof is connected to a discharging side of the pump. The second valve may be disposed at the intake pipe to open and close the intake pipe.

The subsidiary cooling apparatus may further include an exhaust pipe and a third valve. The exhaust pipe may have one end thereof connected between one end of the intake pipe and the second valve. The third valve may be configured to open the exhaust pipe according to the pressure of an inside of the intake pipe.

The subsidiary cooling apparatus may further include a coolant storage container, a supplying pipe, and a fourth valve. The coolant storage may be configured to store the coolant. The supplying pipe may have one end thereof connected between the other end of the intake pipe and the pump while the other end is connected to the coolant storage container. The fourth valve may be disposed at the supplying pipe to open the supplying pipe according to the pressure of an inside of the intake pipe.

The subsidiary cooling apparatus may further include a heat exchanging unit in order for the intake pipe and the discharging pipe to exchange heat with each other.

The coolant storage container may store the coolant in a gaseous state.

A heat delivering member may be disposed between an outer surface of the coil assembly and the cooling pipe so that the heat at the coil assembly is delivered to the cooling pipe.

A plurality of heat delivering members may be disposed about the outer surface and spaced apart from each other.

The superconductive electromagnet apparatus may further include a magnetic resonance imaging apparatus to obtain a cross-sectional image of a living body.

In accordance with another aspect of the present invention, a superconductive electromagnet apparatus includes a coil assembly, a cooling apparatus and a subsidiary cooling apparatus. The coil assembly may be configured to be kept in a cryogenic state. The cooling apparatus may be configured to cool off the coil assembly to a cryogenic state. The subsidiary cooling apparatus may be configured to be connected to the cooling apparatus to operate when an excess amount of heat is generated at the coil assembly for the cooling apparatus to cool off.

As described above, in accordance with one exemplary embodiment of the present invention, a superconductive electromagnet apparatus may evenly cool off the coil assembly in a longitudinal direction thereof through a plurality of cooling pipes connected through the first manifold and the second manifold.

In addition, as described above, in accordance with one exemplary embodiment of the present invention, a superconductive electromagnet apparatus includes a subsidiary cooling apparatus, and thus even when an excess amount of heat is generated for the cooling apparatus to cool off, the superconductive electromagnet apparatus may operate the subsidiary cooling apparatus, thereby maintaining the coil assembly in a cryogenic state in a stable manner.

In addition, since the helium supplied from the helium storage container may be cooled off through the subsidiary cooling apparatus, the helium in a gaseous state may be replenished at the cooling apparatus for use.

BRIEF DESCRIPTION OF THE DRAWINGS

These and/or other aspects of the present invention will become apparent and more readily appreciated from the following description of the exemplary embodiments, taken in conjunction with the accompanying drawings of which.

DETAILED DESCRIPTION OF THE INVENTION

Figure 1:
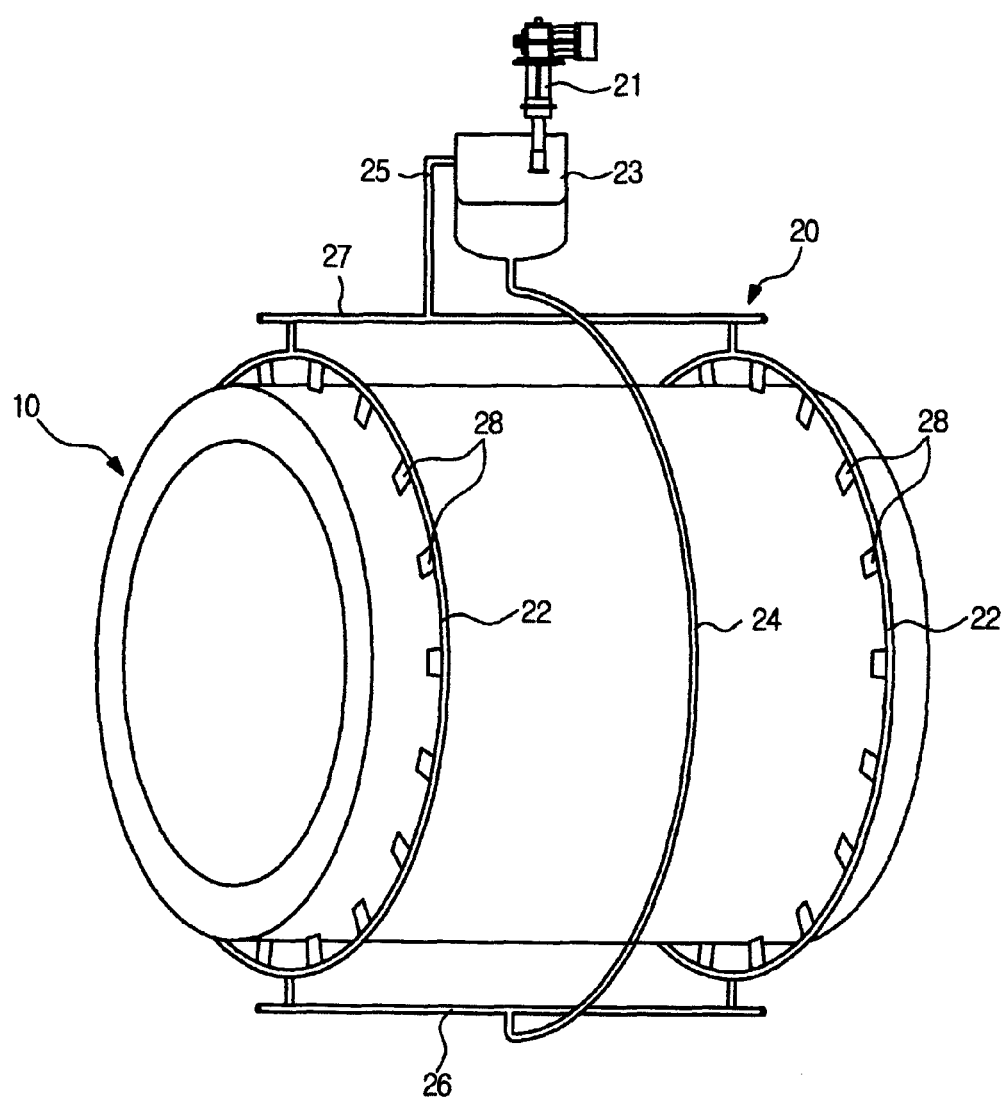
FIG. 1 is a schematic drawing illustrating a coil assembly and a cooling apparatus applied to a superconductive electromagnetic apparatus according to an exemplary embodiment of the present invention.

Reference will now be made in detail to the exemplary embodiments of the present invention, examples of which are illustrated in the accompanying drawings, wherein like reference numerals refer to like elements throughout. Hereinafter, preferred embodiments of the present invention will be described with reference to the accompanying drawings. In the following description, a detailed explanation of known related functions and constructions may be omitted to avoid unnecessarily obscuring the subject matter of the present invention. The present invention may, however, be embodied in many different forms and should not be construed as limited to the exemplary embodiments set forth herein. Also, terms described herein, which are defined considering the functions of the present invention, may be implemented differently depending on user and operator's intention and practice. Therefore, the terms should be understood on the basis of the disclosure throughout the specification. The principles and features of this invention may be employed in varied and numerous embodiments without departing from the scope of the invention.

Furthermore, although the drawings represent exemplary embodiments of the invention, the drawings are not necessarily to scale and certain features may be exaggerated or omitted in order to more clearly illustrate and explain the present invention.

As illustrated in FIG. 1, a superconductive electromagnet apparatus for use in, for example, a magnetic resonance imaging (MRI) apparatus includes a coil assembly 10 to generate a magnetic field when supplied with an electrical current and to operate as a superconductive magnet in a cryogenic state, and a cooling apparatus 20 to cool off the coil assembly 10 so that the coil assembly 10 may be maintained in a cryogenic state. However, it is to be understood that the present invention may be applied to other known apparatus for cooling such apparatus as described herein. Therefore, the present invention is not limited to use with an MRI apparatus.

The coil assembly 10 includes a coil that generates a magnetic field when supplied with an electrical current at an inside region thereof, and is formed to have a cross-section in a shape of a substantially circular ring, and is also formed to have a predetermined length in a direction along an axis thereof.

The cooling apparatus 20 cools off the coil assembly 10 to a cryogenic state using a coolant. In the exemplary embodiment, helium, which maintains a liquid state even in a cryogenic state, is used as the coolant in the cooling apparatus 20. However, other known coolants may be used in addition to or instead of helium.

The cooling apparatus 20 includes a cryogenic cooling device 21 which operates, in a manner known in the art, to cool off the coolant in a gaseous state so that the coolant in the gaseous state may be converted into a liquid state, a plurality of cooling pipes 22 disposed at the coil assembly 10 and which cools off the coil assembly 10 by absorbing heat from the coil assembly 10 while receiving the coolant that is cooled off by the cryogenic cooling device 21, and a buffer chamber 23 configured to receive the coolant, which is gasified, or otherwise changed from a liquid state to a gaseous state, by absorbing heat from the coil assembly 10, and provided with the cryogenic cooling device 21, which is described previously, disposed thereat to cool off the gaseous state coolant into a liquid state, and a plurality of circulation pipes 24 and 25 for circulating the coolant through the cooling pipes 22 and the buffer chamber 23.

Each of the plurality of cooling pipes 22 is formed substantially in a shape of a ring and is disposed at an outer side of the coil assembly 10 while being spaced apart from each other in a longitudinal direction along a longitudinal length of the coil assembly 10. One end of each of the plurality of cooling pipes 22 is connected to a single unit of a first manifold 26, to which the coolant in a liquid state is delivered, while the other end of the plurality of cooling pipes 22 is connected to a single unit of a second manifold 27, to which the coolant in a gaseous state, that is generated at the plurality of cooling pipes 22, is delivered. The first manifold 26 of the exemplary embodiment of the present invention is connected to a lower portion of the plurality of cooling pipes 22 and the second manifold 27 of the exemplary embodiment of the present invention is connected to an upper portion of the plurality of cooling pipes 22 so that the circulation of the coolant may take place through a heat siphon phenomenon.

The plurality of circulation pipes 24 and 25 includes a first circulation pipe 24 having one end thereof connected to the buffer chamber 23 while the other end thereof is connected to the first manifold 26 to guide the coolant, which is cooled off into a liquid state by the cryogenic cooling device 21, from the buffer chamber 23 to the first manifold 26, and a second circulation pipe 25 having one end thereof connected to the second manifold 27 while the other end thereof is connected to the buffer chamber 23 to guide the coolant, which is converted into a gaseous state by absorbing heat from the coil assembly 10, from the second manifold 27 to the buffer chamber 23. Thus, the first manifold 26 distributes and supplies the coolant in a liquid state that is delivered through the first circulation pipe 24 to the plurality of cooling pipes 22, while the second manifold 27 collects the coolant in a gaseous state, which is generated from each of the plurality of cooling pipes 22, and delivers the coolant in a gaseous state to the second circulation pipe 25.

Each of a plurality of heat delivering members 28 is formed from a metal or other known alloys or known materials having a relatively high heat conductivity and is disposed between each of the cooling pipes 22 and an outer surface of the coil assembly 10 so that the heat of the coil assembly 10 may be easily delivered to the cooling pipes 22. Each of the heat delivering members 28 is disposed at an outer surface of the coil assembly 10 while being spaced apart from each other to be thermally and/or physically connected to a corresponding cooling pipe 22 formed in a shape of a ring.

Thus, the coolant in a gaseous state, which is generated at the cooling pipes 22 by absorbing heat from the coil assembly 10 through the heat delivering member 28, moves to the second manifold 27 connected at an upper end of the cooling pipes 22 due to the difference of density with respect to the coolant in a liquid state, and is collected at the second manifold 27. The coolant in a gaseous state is then delivered to the buffer chamber 23 through the second circulation pipe 25, and is cooled off again by the cryogenic cooling device 21 disposed at the buffer chamber 23, and then is converted into a liquid state. In addition, the coolant in a liquid state that is temporarily stored at the buffer chamber 23 is delivered by gravity to the first manifold 26 connected to a lower end of the cooling pipes 22 through the first circulation pipe 24, and is distributed and supplied to the plurality of cooling pipes 22 through the first manifold 26. Alternatively, instead of or in addition to relying on gravity to convey the liquid coolant, the present invention may also include a pump, connected to the cooling pipes 22, the first manifold 26, or other components described herein to pump the liquid coolant therethrough.

As previously discussed above, the coil assembly 10 may be evenly cooled off in a longitudinal direction along a longitudinal length of the coil assembly 10 by having the coolant distributed and supplied to the plurality of cooling pipes 22 through the first manifold 26, with the plurality of cooling pipes 22 distributed in a longitudinal direction along the longitudinal length of the coil assembly 10, as shown in FIG. 1. In addition, the circulation of the coolant at the cooling apparatus 20 occurs due to the difference of density between the coolant in a liquid state and the coolant in a gaseous state, that is, by the heat siphon phenomenon, and thereby the cooling apparatus 20 may be simply structured.

Hereinafter, a magnetic resonance imaging apparatus using a superconductive electromagnet apparatus according to an alternative exemplary embodiment of the present invention will be described in connection with FIG. 2.

Figure 2:
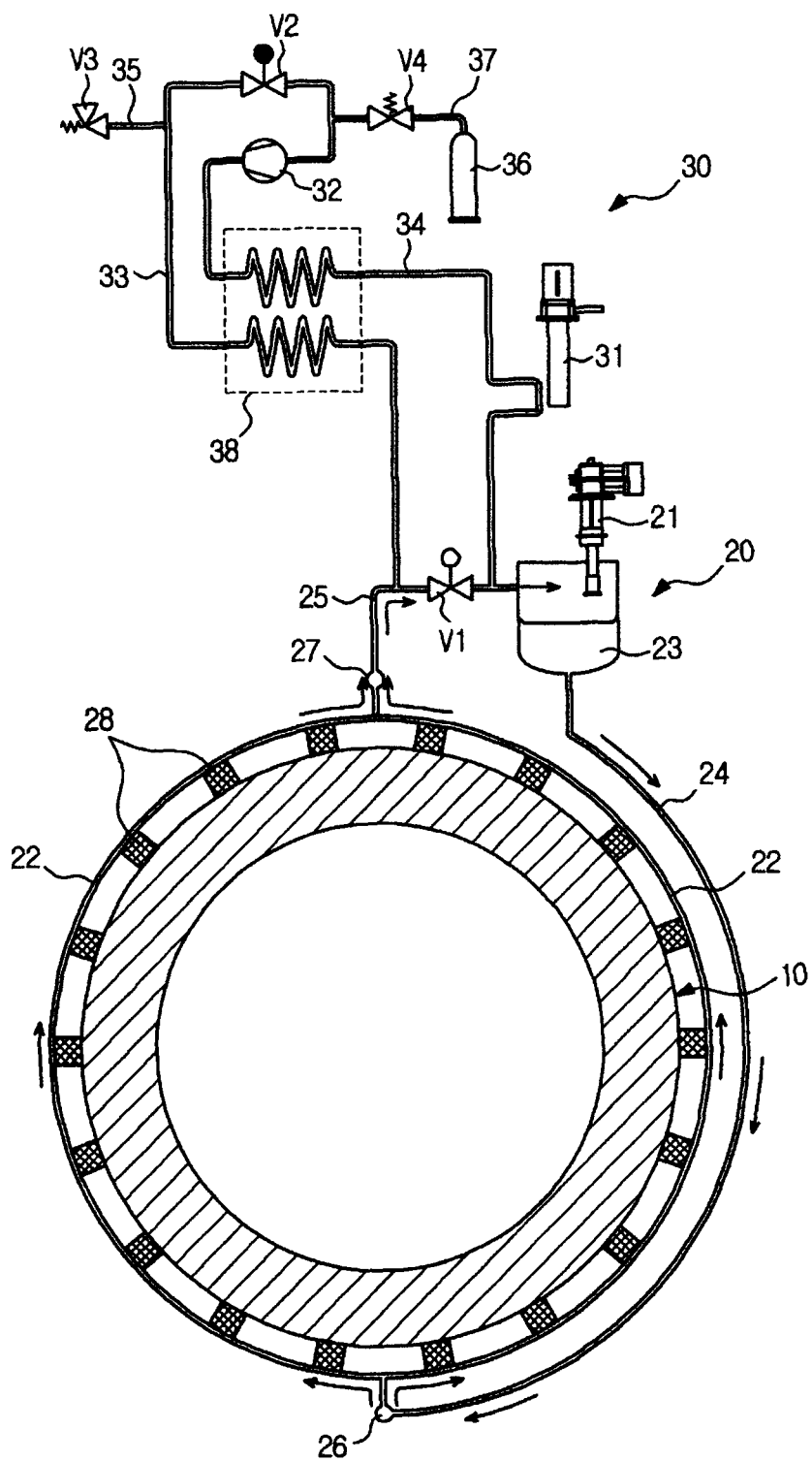
FIGS. 2 to 5 are schematic drawings illustrating the operation of a coil assembly, a cooling apparatus, and a subsidiary cooling apparatus applied to a superconductive electromagnet apparatus according to alternative exemplary embodiment of the present invention.

As shown in FIG. 2, a magnetic resonance imaging apparatus using the superconductive electromagnet apparatus according to an alternative exemplary embodiment of the present invention includes the coil assembly 10 and the cooling apparatus 20 both having the same structure as the magnetic resonance imaging apparatus that is described in the previous exemplary embodiment of the present invention shown in FIG. 1, and further includes a subsidiary cooling apparatus 30 that is used when an excess amount of heat is generated at the coil assembly 10 for the cooling apparatus 20 to cool off.

The subsidiary cooling apparatus 30 according to the alternative exemplary embodiment of the present invention, shown in FIG. 2, is connected to the second circulation pipe 25 of the cooling apparatus 20, cools off the coolant in a gaseous state that is delivered through the second circulation pipe 25, and delivers the cooled coolant again to the second circulation pipe 25. Accordingly, prior to the coolant in a gaseous state being cooled off by the cryogenic cooling device 21 of the cooling apparatus 20, the coolant in a gaseous state is cooled off in advance and then is further cooled off by the cryogenic cooling device 21.

In order to selectively circulate the coolant to the subsidiary cooling apparatus 30, the second circulation pipe 25 of the cooling apparatus 20 is provided with a first valve V1 disposed thereat to selectively open and close the second circulation pipe 25 according to the pressure of the second circulation pipe 25. The first valve V1 may be a smart valve which senses the pressure of the second circulation pipe 25, and which may be set to open and close automatically in response to sensing a predetermined and/or pre-set pressure. Alternatively or in addition, the present invention may include sensors on or in the various pipes and connected to various valves, such as the second circulation pipe 25 and the first valve V1, respectively. The present invention may also include a controller, which may be hardware, a processor, and/or software, connected to both the pipes and the valves to sense the pressure in the various pipes and to open and close a respective value when the sensed pressure attains a predetermined or pre-set pressure. Such smart valves, sensors, and controllers may be implemented in a manner known in the art.

The subsidiary cooling apparatus 30 includes a subsidiary cooling device 31 which operates, in a manner known in the art, to cool off the coolant in a gaseous state, a pump 32 to circulate the coolant in a gaseous state through the subsidiary cooling apparatus 30 by pumping the coolant in a gaseous state, an intake pipe 33 having one end thereof connected to the second circulation pipe 25 between the second manifold 27 and the first valve V1 while the other end of the intake pipe 33 is connected to an intake side of the pump 32 to guide the coolant that is introduced to the pump 32, a discharging pipe 34 having one end connected to the second circulation pipe 25 between the first valve V1 and the buffer chamber 23 while the other end thereof is connected to a discharging side of the pump 32 to guide the coolant that is discharged from the pump 32 again to the second circulation pipe 25, and a second valve V2 disposed at the intake pipe 33 to selectively open and close the intake pipe 33 according to the pressure of an inside of the intake pipe 33. The subsidiary cooling device 31 that is described above is disposed substantially adjacent to the discharging pipe 34 to absorb the heat from the coolant in a gaseous state that passed through the discharging pipe 34. As described herein, the second valve V2 may be a smart valve and/or may be connected to a controller and sensors for controlling the second valve V2 to operate according to the detected pressure relative to a predetermined pressure in a manner known in the art.

The first valve V1 and the second valve V2 operate in an opposite manner relative to each other. That is, when an amount of heat generated at the coil assembly 10 is below the amount of the heat that the cryogenic cooling device 21 is capable of cooling off, the first valve V1 opens the second circulation pipe 25 while the second valve V2 closes the intake pipe 33 so that the coolant may circulate only to the cooling apparatus 20. However, when an amount of heat generated at the coil assembly 10 is above the amount of the heat that the cryogenic cooling device 21 is capable of cooling off into a liquid state, the first valve V1 closes the second circulation pipe 25 while the second valve V2 opens the intake pipe 33 so that the coolant may circulate also to the subsidiary cooling apparatus 30, and thereby the coolant may be cooled off by the subsidiary cooling device 31.

In addition, the subsidiary cooling apparatus 30, according to the alternative exemplary embodiment of the present invention, is configured in a way to discharge the heat when an amount of heat generated at the coil assembly 10 is above the amount of the heat that the cooling apparatus 20 and the subsidiary cooling apparatus 30 are capable of cooling off, and to replenish the coolant again for use.

Accordingly, the subsidiary cooling apparatus 30 includes an exhaust pipe 35 having one end thereof connected to the intake pipe 33 between one end of the intake pipe 33 and the first valve V1 to guide and discharge a portion of the coolant passing through the intake pipe 33, a third valve V3 disposed at the exhaust pipe 35 to open and close the exhaust pipe 35 according to the pressure at an inside of the intake pipe 33, a coolant storage container 36 at which a coolant is stored, a supplying pipe 37 having one end thereof connected to the intake pipe 33 between the other end of the intake pipe 33 and the pump 32 and the other end thereof connected to the coolant storage container 36, and a fourth valve V4 disposed at the supplying pipe 37 to open the supplying pipe 37 according to the pressure of an inside of the intake pipe 33. The first valve V1, the second valve V2, the third valve V3, and the fourth valve V4 open and close according to the pressure of an inside of the second circulation pipe 25. As described herein, any or all of the first value V1, the second valve V2, the third valve V3, and the fourth valve may be smart valves and/or may be connected to a controller and sensors for controlling at least one of the valves V1, V2, V3, and V4 to operate according to detected pressures relative to predetermined pressures in a manner known in the art.

In addition, the subsidiary cooling apparatus 30 further includes a heat exchanging unit 38 for performing a heat exchange between a coolant passing through the intake pipe 33 and a coolant passing through the discharging pipe 34. Thus, the coolant that is supplied from the coolant storage container 36 through the supplying pipe 37 is cooled off by the coolant that passes through the intake pipe 33, and on the other hand, the coolant passing through the intake pipe 33 is heated by the coolant that is supplied from the coolant storage container 36.

As described above, the coolant that is supplied from the coolant storage container 36 is cooled off by the heat exchanging unit 38 and then by the subsidiary cooling device 31 in the process of moving through the discharging pipe 34, and is delivered to the buffer chamber 23, and then is cooled off again by the cryogenic cooling device 21. Thus, even when the coolant in a gaseous state, for example, the helium in a gaseous state, is supplied from the coolant storage container 36, the coolant in a gaseous state may be cooled off into a liquid state through the heat exchanging unit 38, a subsidiary cooling device 31, and the cryogenic cooling device 21, and thereby the coolant storage container 36 may supply the coolant in a gaseous state by storing the coolant in a gaseous state at the coolant storage container 36.

Hereinafter, the operation of the superconductive electromagnetic apparatus and cooling apparatus and method thereof, that is structured as described herein with reference to FIG. 2, will be described in detail.

First, the case in which an amount of heat generated at the coil assembly 10 is below the amount of the heat that the cryogenic cooling device 21 is capable of cooling off is described as follows in connection with FIG. 2.

When heat is generated from the coil assembly 10 during the operation of the superconductive electromagnetic apparatus, the heat is delivered to each of the cooling pipes 22 through the heat delivering member 28, and the heat changes some portion of the coolant in a liquid state at an inside of the plurality of cooling pipes 22 into a gaseous state.

As described above, when an amount of heat generated at the coil assembly 10 is below the amount of the heat that may be cooled off by the cryogenic cooling device 21, the first valve V1 opens the second circulation pipe 25 while the second valve V2 closes the intake pipe 33 so that the coolant circulates only to the cooling apparatus 20.

The coolant in a gaseous state that is generated from each of the cooling pipes 22 is provided with a relatively lower density compared to the coolant in a liquid state, and thus the coolant in a gaseous state moves to be collected at the second manifold 27 that is connected to an upper end of each of the cooling pipes 22, and is introduced to the buffer chamber 23 through the second circulation pipe 25.

In addition, some portion of the coolant in a liquid state at an inside of the buffer chamber 23 moves through the first circulation pipe 24 and the first manifold 26 and is distributed and supplied by gravity to the plurality of cooling pipes 22.

Figure 3:
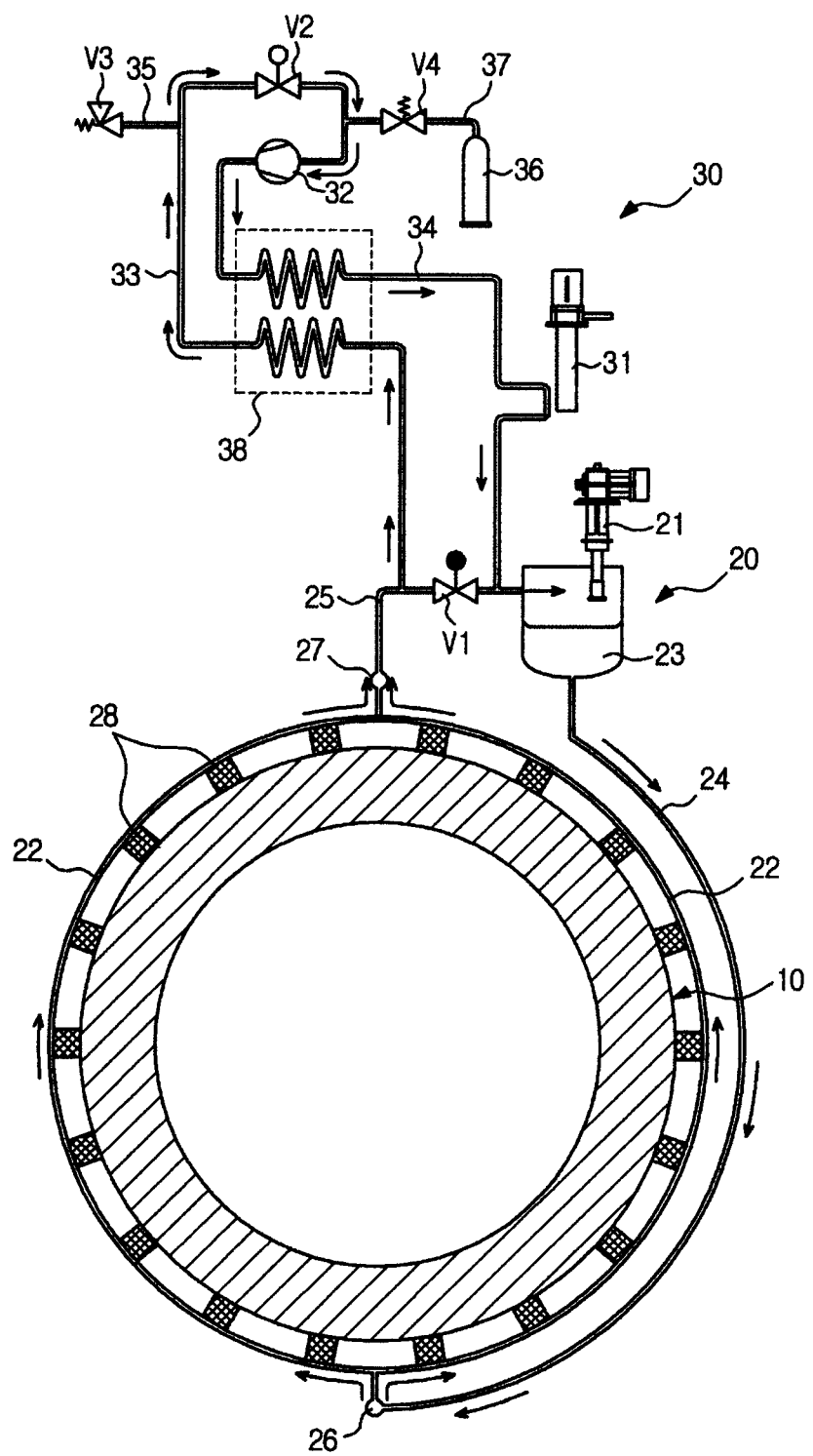

Next, the case in which an amount of heat generated at the coil assembly 10 is above the amount of the heat that the cryogenic cooling device 21 is capable of cooling off, while the amount of heat generated is below the amount of the heat that the cryogenic cooling device 21 and the subsidiary cooling device 31 are capable of cooling off, is described as follows in connection with FIG. 3.

In the case as described above, as illustrated in FIG. 3, the first valve V1 closes the second circulation pipe 25 while the second valve V2 opens the intake pipe 33. In addition, as the pump 32 is operated, the coolant in a gaseous state is introduced to the pump 32 through the intake pipe 33 and then is discharged through the discharging pipe 34.

The subsidiary cooling device 31 according to the alternative exemplary embodiment of the present invention is configured to absorb heat from a coolant in a gaseous state passing through the discharging pipe 34, and thus the coolant in a gaseous state passing through the discharging pipe 34 is first cooled off by the subsidiary cooling device 31 and then is delivered to the second circulation pipe 25 again, and then is introduced to the buffer chamber 23 through the second circulation pipe 25. The coolant in a gaseous state that is cooled off first by the subsidiary cooling device 31 is cooled off again by the cryogenic cooling device 21 at the buffer chamber 23, and is converted into a liquid state.

Figure 4:
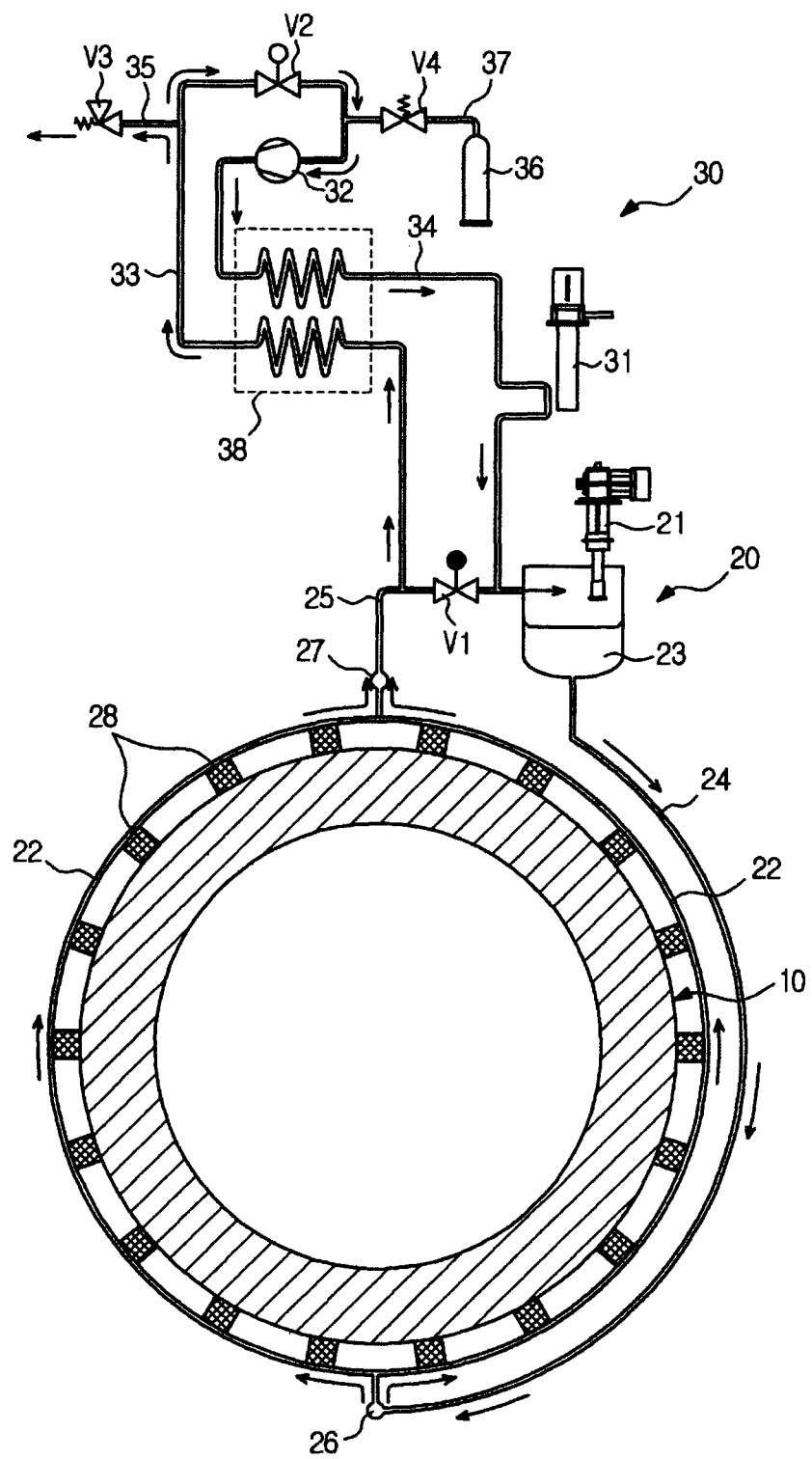

Next, the case in which an amount of heat generated at the coil assembly 10 is above the amount of the heat that the cryogenic cooling device 21 and the subsidiary cooling device 31 are capable of cooling off is described as follows in connection with FIG. 4.

In the case as described above, as illustrated in FIG. 4, the first valve V1 closes the second circulation pipe 25 while the second valve V2 opens the intake pipe 33. In addition, the third valve V3 opens the exhaust pipe 35 to discharge through the exhaust pipe 35 a certain portion of the coolant in a gaseous state, which passes through the intake pipe 33, while the remaining portion of the coolant is introduced to the pump 32 to be discharged through the discharging pipe 34. The coolant in a gaseous state discharged from the pump 32, while passing through the discharging pipe 34, is cooled off first by the subsidiary cooling device 31, and then is delivered to the second circulation pipe 25 to be introduced to the buffer chamber 23 through the second circulation pipe 25. The coolant in a gaseous state, cooled off first by the subsidiary cooling device 31, is cooled off again by the cryogenic cooling device 21 at the buffer chamber 23 and then is converted into a liquid state.

As the cooling by the cryogenic cooling device 21 and the subsidiary cooling device 31 occurs, the pressure of the second circulation pipe 25 is decreased, and when the pressure of the second circulation pipe 25 is decreased below a predetermined level, the third valve V3 closes the exhaust pipe 35 again so that no additional discharging of the coolant occurs.

As the cooling by the cryogenic cooling device 21 and the subsidiary cooling device 31 continues, the pressure of the second circulation pipe 25 is gradually increased, and since some portion of the coolant has been discharged externally through the exhaust pipe 35, the pressure at an inside of the second circulation pipe 25 is decreased below a predetermined level.

Figure 5:
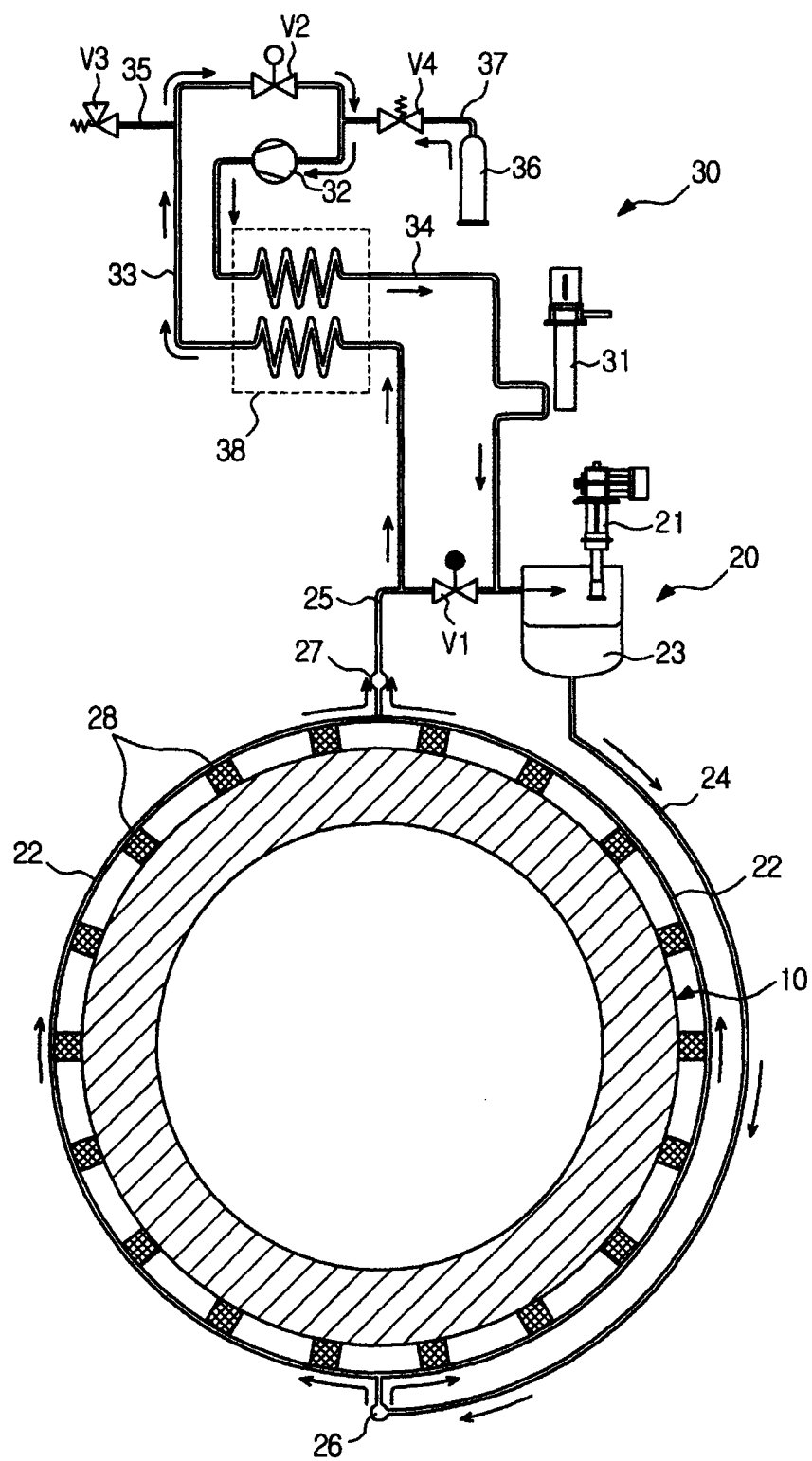

Referring to FIG. 5, the fourth valve V4 opens the supplying pipe 37 when the pressure at an inside of the second circulation pipe 25 is decreased below a predetermined level. Accordingly, the coolant in a gaseous state that is stored at the coolant storage container 36 is delivered to the discharging pipe 34 through the supplying pipe 37, and the coolant supplied from the coolant storage container 36 passes through the heat exchanging unit 38.

At this time, the coolant passing through the intake pipe 33, which is delivered from the cooling pipes 22, has a very low temperature while even in a gaseous state, and on the other hand, the coolant in a gaseous state that is delivered from the coolant storage container 36 is at a level of room temperature; that is, about 21° C. (70° F.) or other comparable temperatures, so that the difference of temperature between the coolant passing through the intake pipe 33 and the coolant delivered from the coolant storage container 36 is very large. Thus, the coolant in a gaseous state delivered from the coolant storage container 36 exchanges heat with the coolant in a gaseous state passing through the intake pipe 33, and therefore is cooled off first.

The coolant in a gaseous state cooled off first in the heat exchange unit 38 is cooled off again in the subsidiary cooling device 31 and then delivered to the buffer chamber 23 through the second circulation pipe 25. The coolant as such in the buffer chamber 23 is finally cooled off in the cryogenic cooling device 21, and so is converted into a liquid state.

According to the exemplary embodiment of the present invention, helium is used as a coolant for the cooling apparatus 20 and the subsidiary cooling apparatus 30, but is not limited hereto, and various materials other than helium may be used as the coolant.

According to the exemplary embodiments of the present invention, a coolant in a liquid state is changed into a gaseous state, or a coolant in a gaseous state is changed into a liquid state by the coil assembly 10 and the cryogenic cooling device 21, and the coolant is configured to circulate through the cooling apparatus 20 according to the change of phase of the coolant, but not limited hereto. For example, the temperature of a coolant may change as a coolant in a gaseous state or in a liquid state is heated by the heat that is generated at the coil assembly 10, and due to the change of the density of the coolant following the change of the temperature, the coolant may circulate through the cooling apparatus 20.

In addition, only the coolant in a gaseous state is configured to be introduced to the second manifold 27 according to the exemplary embodiments of the present invention, but not limited hereto, and the coolant in a mixed state of a gas and a liquid may be introduced to the second manifold 27.

The above-described apparatus and methods according to the present invention, including the various valves, sensors, controllers, and MRI apparatus, can be implemented in hardware, firmware or as software or computer code that can be stored in a recording medium such as a CD ROM, a RAM, a ROM, a floppy disk, DVDs, a hard disk, a magnetic storage media, an optical recording media, or a magneto-optical disk or computer code downloaded over a network originally stored on a remote recording medium, a computer readable recording medium, or a non-transitory machine readable medium and to be stored on a local recording medium, so that the methods described herein can be rendered in such software that is stored on the recording medium using a general purpose computer, a digital computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. In addition, the program may be electronically transferred through any media such as communication signals transmitted by wire/wireless connections, and their equivalents.

Although a few exemplary embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A superconductive electromagnet apparatus, comprising:
   a coil assembly receives an electrical current and generates a magnetic field, and is configured to be kept at a cryogenic state, and
   a cooling apparatus configured to cool off the coil assembly to the cryogenic state,
   wherein the cooling apparatus comprises a plurality of cooling pipes disposed at the coil assembly and supplied with a coolant to absorb heat generated at the coil assembly, a first manifold configured to distribute and supply the coolant to the plurality of cooling pipes, and a second manifold supplied with the coolant from the plurality of cooling pipes.

2. The superconductive electromagnet apparatus of claim 1, wherein the first manifold is connected to a lower portion of the plurality of cooling pipes, and the second manifold is connected to an upper portion of the plurality of cooling pipes.

3. The superconductive electromagnet apparatus of claim 1, wherein the cooling apparatus further comprises:
   a buffer chamber at which the coolant delivered from the second manifold is temporarily stored; a cryogenic cooling apparatus disposed at the buffer chamber to cool off the coolant; a first circulation pipe to guide the coolant from the buffer chamber to the first manifold; and a second circulation pipe to guide the coolant from the second manifold to the buffer chamber.

4. The superconductive electromagnet apparatus of claim 3, further comprises a subsidiary cooling apparatus connected to the second circulation pipe, wherein the cooling apparatus comprises a first valve disposed at the second circulation pipe, and the subsidiary cooling apparatus comprises: a subsidiary cooling device to cool off the coolant, a pump to pump the coolant, an intake pipe having one end thereof connected to the second circulation pipe between the first valve and the second manifold while the other end thereof is connected to an intake side of the pump, a discharging pipe having one end thereof connected to the second circulation pipe between the first valve and the buffer chamber while the other end thereof is connected to a discharging side of the pump, and a second valve disposed at the intake pipe to open and close the intake pipe.

5. The superconductive electromagnet apparatus of claim 4, wherein the subsidiary cooling apparatus further comprises: an exhaust pipe having one end thereof connected between one end of the intake pipe and the second valve; and a third valve configured to open the exhaust pipe according to the pressure of an inside of the intake pipe.

6. The superconductive electromagnet apparatus of claim 5, wherein the subsidiary cooling apparatus further comprises: a coolant storage container to store the coolant; a supplying pipe having one end thereof connected between the other end of the intake pipe and the pump while the other end is connected to the coolant storage container; and a fourth valve disposed at the supplying pipe to open the supplying pipe according to the pressure of an inside of the intake pipe.

7. The superconductive electromagnet apparatus of claim 6, wherein the subsidiary cooling apparatus further comprises a heat exchanging unit for the intake pipe and the discharging pipe to exchange heat with each other.

8. The superconductive electromagnet apparatus of claim 6, wherein the coolant storage container stores the coolant in a gaseous state.

9. The superconductive electromagnet apparatus of claim 1, further comprising a heat delivering member disposed between an outer surface of the coil assembly and at least one of the plurality of cooling pipes so that the heat at the coil assembly is delivered to the at least one of the cooling pipes.

10. The superconductive electromagnet apparatus of claim 9, wherein the heat delivering member includes a plurality of heat delivering members disposed about the outer surface and spaced apart from each other.

11. The superconductive electromagnet apparatus of claim 1, further comprising:

a magnetic resonance imaging apparatus, using the coil assembly, to obtain a cross-sectional image of a living body.

12. A superconductive electromagnet apparatus, comprising:

a coil assembly receives an electrical current and generates a magnetic field, and is configured to be kept at a cryogenic state, a cooling apparatus configured to cool off the coil assembly to the cryogenic state, and a subsidiary cooling apparatus connected to the cooling apparatus to operate when an excess amount of heat is generated at the coil assembly for the cooling apparatus to cool off.

13. The superconductive electromagnet apparatus of claim 12, wherein the cooling apparatus comprises a plurality of cooling pipes disposed at the coil assembly and supplied with the coolant to absorb heat generated at the coil assembly, a first manifold connected to a lower portion of the plurality of cooling pipes, a second manifold connected to an upper portion of the plurality of cooling pipes, a buffer chamber at which the coolant delivered from the second manifold is temporarily stored, a cryogenic cooling device disposed at the buffer chamber to cool off the coolant, a first circulation pipe to guide the coolant from the buffer chamber to the first manifold, and a second circulation pipe to guide the coolant from the second manifold to the buffer chamber.

14. The superconductive electromagnet apparatus of claim 13, wherein the cooling apparatus comprises a first valve disposed at the second circulation pipe, and the subsidiary cooling apparatus comprises a subsidiary cooling device to cool off the coolant, a pump to pump the coolant, an intake pipe having one end thereof connected to the second circulation pipe between the first valve and the second manifold while the other end thereof is connected to an intake side of the pump, a discharging pipe having one end thereof connected to the second circulation pipe between the first valve and the buffer chamber while the other end thereof connected to a discharging side of the pump, and a second valve disposed at the intake pipe.

15. The superconductive electromagnet apparatus of claim 14, wherein the subsidiary cooling apparatus further comprises an exhaust pipe having one end thereof connected between one end of the intake pipe and the second valve, and a third valve to open the exhaust pipe according to the pressure of an inside of the intake pipe.

16. The superconductive electromagnet apparatus of claim 15, wherein the subsidiary cooling apparatus further comprises a coolant storage container, a supplying pipe having one end thereof connected between the other end of the intake pipe and the pump while the other end is connected to the coolant storage container, and a fourth valve disposed at the supplying pipe to open the supplying pipe according to the pressure of an inside of the intake pipe.

17. The superconductive electromagnet apparatus of claim 16, wherein the subsidiary cooling apparatus further comprises a heat exchanging unit for the intake pipe and the discharging pipe to exchange heat with each other.

18. The superconductive electromagnet apparatus of claim 12, further comprising a magnetic resonance imaging apparatus, using the coil assembly, to obtain a cross-sectional image of a living body.

* * * * *